United States Patent [19]

Dandamudi

[11] 3,995,020

[45] Nov. 30, 1976

[54] RADIOACTIVE ERBIUM-165 COMPLEXES AND METHODS OF PREPARATION AND USE THEREOF

[75] Inventor: Vishnuvardhana Rao Dandamudi, Dover, N.J.

[73] Assignee: Albert Einstein College of Medicine of Yeshiva University, Bronx, N.Y.

[22] Filed: May 23, 1975

[21] Appl. No.: 580,210

[52] U.S. Cl. .............................. 424/1.5; 260/429 R; 424/1

[51] Int. Cl.$^2$ .................. A61K 29/00; G01T 1/161; G01T 1/16; G21H 5/02

[58] Field of Search............. 424/1, 1.5; 260/429 R, 260/429.2; 176/10, 14, 16

[56] References Cited

OTHER PUBLICATIONS

Bredenfeld et al., Chemical Abstracts, vol. 81, No. 14, Oct. 7, 1974, p. 344, abstract No. 82945w.
Ternovaya et al., Chemical Abstracts, vol. 78, No. 10, Mar. 12, 1973, p. 309, abstract No. 62983s.
Pyatnitskii et al., Chemical Abstracts, vol. 77, No. 4, July 24, 1972, p. 423, abstract No. 25456f.
Ternovaya et al., Chemical Abstracts, vol. 78, No. 18, May 7, 1973, p. 308, abstract No. 115898b.
Isobe et al., Chemical Abstracts, vol. 81, No. 24, Dec. 16, 1974, p. 554, abstract No. 161500a.
Glasstone et al., *Introduction to Nuclear Reactor Engineering*, D. Van Nostrand Co., Inc., Princeton, N.J., 1963, p. 3.
McLennan et al., Nature, vol. 136, Nov. 23, 1935, pp. 831–832.

*Primary Examiner*—Benjamin R. Padgett
*Assistant Examiner*—Christine M. Nucker
*Attorney, Agent, or Firm*—Bierman & Bierman

[57] ABSTRACT

Complexes based on erbium-165 are disclosed. Such materials, particularly the citrate, are useful for imaging of cardiac infarcts and tumors, especially adenocarcinomas and sarcomas. Excellent resolution with low energy photons is obtained, particularly with the use of multiwire proportional cameras.

5 Claims, No Drawings

RADIOACTIVE ERBIUM-165 COMPLEXES AND METHODS OF PREPARATION AND USE THEREOF

The present invention is directed to complexes of erbium-165 which are useful in pharmaceutical applications for radioactive scanning and evaluation of various organ and body functions. More specifically, the invention is directed to a 165 erbium-citrate which is useful in imaging of cardiac infarcts and tumors.

The multiwire proportional camera (MWPC) developed by Kaufman et al (Performance of a Pressurized Xenon-filled Multiwire Proportional Chamber, IEEE Trans. Nucl.Sci. NS-20:333, 1972) has a maximum detection efficiency for photons of energy just above the xenon K-edge (35 keV). It was shown by them that as the energy of the photon increases, not only the detection efficiency drops rapidly but also the spatial resolution deteriorates. For these reasons, radionuclides which emit photons of energy around 40 keV but not less than 35 keV are extremely useful if they are clinically valuable. The relatively simple and inexpensive MWPC can play an increasingly significant role in nuclear medicine if radionuclides and pharmaceuticals particularly suitable for this imaging device are studied and developed. I have found that erbium-165 is well suited to this purpose. It has a half-life of about 10 hours. This is long enough to permit normal shipping and handling and short enough to prevent any serious damage to healthy tissue, even in comparatively large doses. The dose from $^{165}$Er to the whole body is 0.12 rads and to the skeleton 0.33 rads, whereas from $^{99m}$Tc the whole-body dose is 0.15 rads and the skeleton receives 0.45 rads for an administered dose of 10 mCi in each case. Thus, the absorbed dose is about 25% less with $^{165}$Er, which has a physical half-life longer than that of $^{99m}$Tc.

Moreover, erbium-165 has the ability to concentrate in cardiac infarcts and tumors, particularly adenocarcinomas and sarcomas. It emits photons of 48 and 54 keV. These low energy photons provide additional safety for the patient as well as improved resolution, especially with the MWPC.

EXAMPLE I

About 8 mg of stable erbium-164 in the form of $Er_2O_3$ (available from Oak Ridge National Laboratories) are irradiated with $6.7\times10^{13}$ neutrons/cm$^2$/second. After 16 hours of radiation about 50mCi of erbium-165 is obtained and is dissolved in concentrated nitric acid to dryness. 10% citric acid is and allowed to dry to obtain the erbium citrate.

There are two other radionuclides produced during this process due to impurities in stable $^{164}$Er. These are $^{169}$Er and $^{171}$Er with 9.4 days and 7.5 hr half-life, respectively. The radionuclide $^{169}$Er is a pure beta-emitter with an end-point energy of about 0.34 MeV while $^{171}$Er emits beta-gamma radiations. There was approximately 10% of $^{169}$Er and 5% of $^{171}$Er in the amount we produced. These impurities are not desirable for clinical use but the resulting radiations do not interfere with animal or phantom studies. With further enrichment of stable erbium-164, the amounts of these impurities can be reduced.

EXAMPLE II

About 30 $\mu$Ci of the $^{165}$Er-citrate of Example I was injected intraperitoneally into a mouse with an implanted tumor in the right thigh. After 3 hours, a scintillation image of the mouse was taken using a pinhole collimator. Surprisingly, excellent resolution was obtained with this low energy level emitter, even with a standard scintillation camera.

Similar results were obtained in imaging cardiac infarcts in dogs. The characteristics of the erbium-165 isotope make it eminently suitable for safe, low level imaging (especially with the MWPC), while also providing excellent resolution.

While only one specific embodiment of this invention has been disclosed, such changes in variations as to be apparent to the person having ordinary skill in the art may be made without departing from the scope or spirit thereof. For example, numerous other complexes of erbium-165 can be used in place of the citrate. The choice depends upon pharmacological considerations well known to those skilled in the art. Chelating agents are useful; especially diethylenetriamine penta-acetic acid and those in the same category. Also, organic and inorganic Er complexing agents will be operable in the present invention.

These are generally known to those of ordinary skill in the art. Suitable complexing agents are, for example, ethylenediaminetetraacetic acid, nitrilopropionic acid, N-2, hydroxyethyliminodiacetic acid, tartaric acid, human serum albumin, gluconates, polyphosphates, pyrophosphates, phosphonates, dimercaptosuccinic acid, malonic acid, thiocyanates, oximes and sulfonic acid derivatives thereof, naphthalene sulfonic acid derivatives, ethylene diamine, penicillamine, and tetracycline.

Since the complexes will be used inside the body, all materials used must, of course, be pharmaceutically acceptable. The dosage can vary widely as is known to those having ordinary skill in the art. It is also worth noting that the radionuclide $^{165}$Tm, the parent of $^{165}$Er, has a physical half-life of 30 hr and therefore offers the possibility for a generator.

What is claimed is:

1. A method of radioactively scanning portions of the body of a warm blooded animal comprising
   a. administering a complex of radioactive erbium-165 and a pharmaceutically acceptable complexing agent to said animal;
   b. permitting said complex to be distributed in said body; and
   c. exposing means for sensing radioactivity to said portions.

2. A method according to claim 1 wherein said complexing agent is a chelating agent.

3. A method according to claim 1 wherein said complexing agent is taken from the class consisting of diethylenetriaminepentaacetic acid; ethylenediaminetetraacetic acid; nitrilopropionic acid; N-2-hydroxyethyliminodiacetic acid; citric acid; tartaric acid; human serum albumin; gluconates; polyphosphates; pyrophosphates; phosphonates; dimercaptosuccinic acid; malonic acid; thiocyanates; oximes and sulfonic acid derivatives thereof; naphthalene sulfonic acid derivatives; ethylene diamine; penicillamine; and tetracycline.

4. A method according to claim 1 wherein said complex is $^{165}$Er-citrate and said portions comprise tumors and/or infarcts.

5. A method according to claim 1 wherein said complex is administered intraperitoneally.

* * * * *